United States Patent [19]

Heberer et al.

[11] Patent Number: 5,095,143

[45] Date of Patent: Mar. 10, 1992

[54] METHOD FOR INCREASING THE EFFICIENCY OF LIQUID PHASE OXIDATION REACTIONS

[75] Inventors: Daniel L. Heberer, Shorewood; Paul R. Schiller; Virginia R. Seemann, both of Naperville; Michael J. Yerkes, River Forest, all of Ill.

[73] Assignee: Amoco Corporation, Chicago, Ill.

[21] Appl. No.: 537,376

[22] Filed: Jun. 13, 1990

[51] Int. Cl.⁵ .................... C07C 51/265; C07C 27/12; C07C 29/48

[52] U.S. Cl. ................................. 562/416; 260/413; 562/412; 562/417; 562/421; 562/531; 562/533; 562/536; 562/538; 562/544; 562/548; 562/889; 568/320; 568/569; 568/570; 568/571; 568/577; 568/771; 568/802; 568/910

[58] Field of Search .............. 562/416, 417, 421, 531, 562/533, 536, 538, 548, 544, 889; 568/320, 569, 570, 571, 577, 771, 802, 910; 260/413

[56] References Cited

U.S. PATENT DOCUMENTS 4,764,639  8/1988  Schammel .......................... 562/416

OTHER PUBLICATIONS

Oldshue, Ph.D. *Fluid Mixing Technology*, (1983), Chemical Engineering, McGraw-Hill Pub. Co., pp. 384–389.

*Primary Examiner*—Jose G. Dees
*Assistant Examiner*—Vera C. Clarke
*Attorney, Agent, or Firm*—Thomas E. Nemo; William H. Magidson; Ralph C. Medhurst

[57] ABSTRACT

A method to oxidize an oxidizable component in a liquid phase with an oxygen-containing gas is disclosed. The method comprises mixing the liquid phase and gas phase in a reactor with a rotating agitator element operated at constant power.

12 Claims, No Drawings

METHOD FOR INCREASING THE EFFICIENCY OF LIQUID PHASE OXIDATION REACTIONS

FIELD OF THE INVENTION

This invention relates generally to the improvement of liquid phase oxidation reactions. More particularly, the present invention concerns a method for increasing the efficiency of an oxidation reaction wherein an alkylaromatic hydrocarbon is oxidized in the liquid phase in the presence of a heavy-metal oxidation catalyst and a source of oxygen-containing gas.

BACKGROUND OF THE INVENTION

Liquid phase oxidation reactions of inorganic and particularly organic compounds using air or other source of molecular oxygen are important industrial chemical reactions. In these oxidation reactions the organic or inorganic compound undergoing oxidation is dissolved in a suitable reaction solvent, with or without an oxidation catalyst, and air or other oxygen-containing gas is typically sparged into the reaction mixture. However, for those organic compounds that are liquid at the oxidation reaction conditions a solvent is not always necessary. Utilization of air as a reactant to effect a chemical transformation has a readily apparent large economic incentive because the air need only be compressed and then injected or sparged into the reaction mixture. Consequently, when air can be used to selectively convert a given inorganic or organic compound to another useful compound, it is usually economically advantageous to do so. However, the transfer of oxygen from the vapor phase to the liquid phase is usually a critical part of any commercial liquid phase oxidation reaction. Mixing is the principal method for promoting the mass transfer of oxygen to the liquid phase in most liquid phase oxidation reactions where air or other forms of gaseous oxygen is the source of oxygen for the oxidation reaction. Many, if not all, of the problems associated with mixing a liquid phase oxidation reaction are present during the liquid phase oxidation of an alkylaromatic hydrocarbon to the corresponding aromatic carboxylic acid.

The liquid phase, heavy-metal catalyzed oxidation of an alkylaromatic hydrocarbon compound to the corresponding aromatic carboxylic acid is a reaction of particular commercial importance. Commodity aromatic carboxylic acids such as terephthalic acid, isophthalic acid and trimellitic anhydride are produced by one or more of such liquid phase oxidation processes in quantities of millions and, in some cases, billions of pounds per year. One such liquid phase oxidation process, the so-called Mid-Century Oxidation process, is a particularly suitable process for preparing aromatic carboxylic acids. In this process, as disclosed in Saffer and Barker, U.S. Pat. No. 2,833,816, a catalyst comprising cobalt, manganese and bromine components, a low-molecular weight aliphatic carboxylic acid reaction solvent and an oxygen-containing gas as a source of oxygen are used in combination to oxidize an alkyl group on an alkylaromatic hydrocarbon molecule to a carboxylic acid group. The oxygen-containing gas, typically air, is introduced into the reaction mixture and reacts with the alkylaromatic hydrocarbon in conjunction with the oxidation catalyst. Depending on the particular aromatic carboxylic acid produced by this process and on the conditions used for the oxidation reaction, the aromatic carboxylic acid may or may not be soluble in the reaction mixture. If insoluble or only partly soluble, the typically solid aromatic carboxylic acid will be present in the oxidation reaction mixture. Consequently, these liquid phase oxidation reaction mixtures always contain a gas phase and, in addition, may contain a solid phase as well.

In order to promote the contact of the oxygen-containing gas with the liquid phase components and, if present, to maintain the solid aromatic carboxylic acid suspended in the reaction mixture, these oxidation reaction mixtures are typically well mixed using a suitable agitator. Usually, these agitators comprise a rotating impeller located within the reaction mixture. Efficient mixing disperses the oxygen-containing gas thereby providing improved gas-liquid contact and improved mass transfer of the gas into the liquid phase where the oxidation reaction is occurring. For example, when mixing is inadequate, portions of the reaction mixture, so-called "pockets", have an insufficient concentration of oxygen. It is speculated that within these oxygen-deficient pockets the high molecular weight impurities or other reaction side products are formed that detract from the ultimate quality of the product aromatic carboxylic acid. Additionally, an increase in the concentration of oxygen in the liquid phase resulting from improved mass transfer and gas-liquid contact generally improves the rate of the oxidation reaction resulting in shorter reaction time and greater production rates for the aromatic carboxylic acid.

In known processes for the oxidation of alkylaromatics a specific, fixed mixing speed, i.e. the rotational speed of the agitator used for mixing the oxidation reaction, is selected. Speed selection is based on the estimated maximum density of the oxidation reaction mixture utilizing the accepted horsepower mixing equation:

$$Hp = \frac{(\text{power no.})\,(\text{density})\,(\text{rpm})^3\,(\text{diameter})^5}{1.523 \times 10^{13}}$$

Hp = mixing horsepower
power no. = constant for a given system
density = density of reaction mixture or other composition being mixed
rpm = agitator speed, revolutions per minute
diameter = diameter of agitator impeller Assuming the power number and impeller diameter remain constant it is apparent that mixing horsepower is proportional to the product of the agitator speed to the third power and the density value. Consequently, if the density of the reaction mixture varies while at a constant agitator speed, the horsepower delivered to the reaction mixture varies accordingly.

During the oxidation of an alkylaromatic hydrocarbon to a carboxylic acid the density of the reaction mixture does change. Change in density arises due to factors such as changing reaction temperature, pressure, planned changes in the rate of addition of the oxygen-containing gas, and due to the production of the oxygenated aromatic carboxylic acid product. Furthermore, there may be a fluctuation in reaction mixture density due to changes in the rate of addition of the oxygen-containing gas to the reaction mixture as may be caused, for example, by inadvertent fluctuations in the output of the compressor used for supplying the oxygen-containing gas to the oxidation reactor. Under conditions where the oxygen-containing gas is being introduced to the reaction mixture, commonly referred to as the gassed state, the density of an oxidation reaction mixture may be only one half of the density of the reaction mixture in the ungassed state. Even when fully gassed, an oxidation reaction mixture may vary in density by as much as 7% from the beginning of the oxidation reaction to the end of the reaction due to the aforementioned factors such as reaction mixture composition, reaction temperature, and scheduled changes in the rate of addition of the oxygen-containing gas.

Due to the use of a fixed agitator speed in prior processes and due to the changing density of the alkylaromatic hydrocarbon oxidation reaction mixture, the agitator speed is set in prior processes using the maximum estimated density of the reaction mixture. Otherwise, assuming full utilization of the capacity, i.e. fully loaded condition, of the mixing motor used for rotating the agitator, the motor would overload when the reaction mixture density increases. Particularly drastic results would occur if the gas flow were to greatly decrease or stop since this would produce an abrupt change in density and, consequently, a severe overload on the motor. Furthermore, if the motor overloads and mixing stops product quality may be greatly reduced requiring the disposal of the contents of the reactor. Potentially explosive conditions could also develop.

Therefore, when employing the standard, fixed agitator speed method of mixing a liquid phase oxidation reaction, full mixing capacity is not utilized throughout the course of the oxidation reaction. During the phase of the oxidation reaction where the density is below maximum, the power delivered to the oxidation reaction is below the maximum available or, in other words, the mixing speed is below that which is possible at that particular reaction mixture density.

A new method for increasing the efficiency of a liquid phase oxidation reaction and, in particular, the oxidation of an alkylaromatic hydrocarbon to an aromatic carboxylic acid by increasing the efficiency of the mixing of the oxidation reaction mixture would be highly advantageous. The present invention provides such a method.

SUMMARY OF THE INVENTION

Provided is a method to oxidize an oxidizable component in a liquid phase with an oxygen-containing gas phase component comprising mixing the liquid phase and the gas phase components in a reactor with a rotating agitator element wherein said rotating agitator is operated at substantially constant power.

The method of this invention is also an improved method for mixing an oxidation reaction mixture comprising a liquid phase component and a gas phase component wherein the gas phase component comprises an oxygen-containing gas, the improvement comprising mixing said reaction mixture with a rotating agitator element located within said reaction mixture, said agitator element being rotated by a means for rotating said agitator at variable speeds during said mixing such that constant power is delivered to said rotating agitator element, and wherein at least one liquid phase component is oxidized.

In particular, the oxidation of alkylaromatics to corresponding aromatic carboxylic acids in the liquid phase in the presence of an oxidation catalyst and a source of oxygen-containing gas is improved by providing for improved mixing during the oxidation reaction. Improved mixing is provided by maintaining constant or substantially constant power to the rotating agitator used to mix the reaction mixture. Rather than maintaining constant agitator speed, the agitator speed varies and constant agitator power is maintained. Constant or substantially constant power rather than constant agitator stirring speed allows for maximum stirring speeds throughout the course of the oxidation reaction mixture wherein the density of the reaction mixture or other reaction mixture variable is changing.

More specifically, the presently contemplated method is a method for oxidizing an alkylaromatic hydrocarbon to a corresponding aromatic carboxylic acid in the liquid phase under oxidation reaction conditions comprising, introducing into a suitable oxidation reactor a reaction mixture comprising a suitable reaction solvent, an oxidation catalyst comprising heavy-metal components, said alkylaromatic hydrocarbon and an oxygen-containing gas; mixing said reaction mixture; and maintaining said reaction mixture at a temperature and for a time sufficient to convert at least a portion of said alkylaromatic hydrocarbon to said aromatic carboxylic acid; wherein said mixing comprises rotating an agitator element located within said reaction mixture at a substantially constant power during at least a substantial portion of said addition of said oxygen-containing gas.

A surprising feature of the present method is the ability to mix a liquid phase oxidation reaction mixture at greater agitation speeds and thereby provide for improved gas-liquid contact between the oxygen-containing gas and the liquid oxidation reaction mixture resulting in an improved oxidation reaction and improved products.

Further other features and embodiments and the like of this invention will become apparent to those skilled in the art from the present description of this invention.

DETAILED DESCRIPTION OF THE PREFERRED EMBODIMENTS

The method of this invention is applicable to liquid phase reactions wherein a gas phase is present and, preferably, wherein the gas phase is molecular oxygen or a gas containing molecular oxygen. For example, and without intending to limit the scope of the present invention, the disclosed method is useful for liquid phase oxidation reactions such as the oxidation of aldehydes to carboxylic acids as in the oxidation of acetaldehyde to acetic acid and acetic anhydride, the oxidation of butane or naphtha to acetic acid, the oxidation of a hydrocarbon such as cyclohexane to cyclohexanol and cyclohexanone or the oxidation of a higher molecular weight paraffin to a fatty acid, the oxidation of isobutane to t-butyl hydroperoxide, the oxidation of ethylbenzene to ethylbenzene hydroperoxide, cumene to cumene hydroperoxide and sec-butylbenzene to sec-butylbenzene hydroperoxide, the oxidation of isopropyl alcohol to hydrogen peroxide and acetone, and the oxidation of an alcohol to a carboxylic acid such as the oxidation of ethanol to acetic acid. All of these oxidation reactions including the oxidation reaction of an alkylaromatic hydrocarbon to an aromatic carboxylic acid as described below can be accomplished in the liquid phase using air or other oxygen-containing gas as a source of molecular oxygen.

According to the preferred method of the present invention an alkylaromatic hydrocarbon is oxidized to its corresponding aromatic carboxylic acid in the liquid phase in a suitable reactor vessel and in the presence of a reaction solvent, an oxidation catalyst comprising heavy-metal components and an oxygen-containing gas. The reaction reaction mixture is mixed by a suitable agitator element located within the reaction mixture such that the agitator is rotated within the reaction mixture. According to the method of this invention the agitator is rotated at constant or substantially constant power for at least a substantial portion of the time during which the oxygen-containing gas is being added to the oxidation reaction mixture. Preferably, the agitator is being rotated at constant or substantially constant power for the total time during which the oxygen-containing gas is being added to the oxidation reaction mixture.

Although a wide variety of different configurations and types of reaction vessels and agitators, such as side, bottom and top entry agitators are suitable for oxidizing alkylaromatics, preferably the reactor vessel of this method comprises a vertically disposed elongated reaction vessel having a substantially cylindrical sidewall and having the agitator mounted for rotation within the vessel along the axis of the vessel. The reactor vessel is equipped with a means for adding reactants and means for removing products, heating and/or cooling means, means for introducing the oxygen-containing gas, vent gas outlet and means for controlling reaction pressure. The agitator comprises a rotatable shaft having one or more impellers fixedly mounted thereto. Preferably there are two impellers. The impellers may be of any type including the standard flat blade with or without a disk, propeller, axial flow, i.e. pitched-blade impellers, and spiral impellers. Preferably there are 2 to 6 blades per flat blade, propeller-type and pitched-blade impeller.

The means for rotating the agitator in the method of this invention comprises any suitable means for rotating the agitator at variable speeds and, therefore, the ability according to the method of this invention to rotate the impeller at a constant or substantially constant power. For example, without intending to limit the means for providing variable speed stirring, such rotating means includes hydraulic, steam-driven, electric motor and mechanical means. Importantly, the means for rotating the agitator must be able to provide variable speeds as the density or viscosity of the mixture varies so that the mixing speed will decrease or increase so that constant or substantially constant power to the agitator can be maintained. Suitable types of variable-speed devices are described in Oldshue, Fluid Mixing Technology, McGraw-Hill Publications Co., N.Y., N.Y., 1983, pages 384–389. Most preferably, the means for rotating the agitator comprises a variable speed electric motor wherein the speed of the motor is controlled by varying the frequency of the alternating current supplied to the motor. Suitable variable speed controls for electric motors are available from Westinghouse Corporation. An electric motor is particularly suitable for the method of this invention because it is possible to maintain a constant or substantially constant amperage to the electric motor. Amperage is proportional to delivered horsepower according to the following equation:

$$I \text{ (amperage)} = \frac{(Hp)(0.7463 \times 10^3)}{(1.73)(\text{voltage})(\text{power factor})(\text{motor efficiency})}$$

Therefore, by maintaining constant amperage constant power will be maintained as it is the agitator speed that will vary as the density or other reaction mixture variable fluctuates. One method for maintaining constant or substantially constant amperage to the electric motor comprises manually controlling the speed of the variable speed electric motor. Most preferably, the maintenance of the constant amperage is provided for automatically. When the amperage is controlled automatically, a specific amperage is set and the reaction proceeds under constant or substantially constant power with the agitator speed adjusting accordingly. In one suitable procedure for automatically maintaining constant or substantially constant amperage, the three-phase power line to the variable speed electric motor is equipped with a 0–5 amp current transmitter device for sensing the current supplied to the motor. The output from the current transmitter is converted to a 4–20 milliamp signal. This signal, which is directly proportional to the motor current, is compared to the desired amperage set point in the process control computer and the frequency of the current to the variable speed motor is increased or decreased so as to maintain constant the set point amperage. The motor speed is, in turn, proportional to the frequency of the current. Additionally, some variable speed motor controls provide a 4–20 milliamp signal proportional to motor amp draw and, therefore, a current transmitter is not required. By either the manual or automatic method the set point amperage should be maintained in the range of about 95% to about 105% of the set point amperage and preferably in the range of about 97% to about 103% of the set point amperage, more preferably substantially constant and most preferably constant.

Preferably, the power level selected should be the power that fully loads or nearly fully loads the electric motor or other means for rotating the agitator. However, the power level may suitably be about 60% to about 100% maximum power, and more suitably about 80% to about 100% maximum power of the electric motor or other means for rotating the agitator. By fully loading the motor maximum use of the available mixing power is realized. Other factors, however, such as critical agitator shaft speeds, i.e., the speeds at which destructive resonance develops in the agitator shaft, costs, equipment wear, etc. need to be taken into consideration when selecting the stirring power level. Maximum loading, however, is preferable.

The alkylaromatic hydrocarbon oxidized by the method of this invention to an aromatic carboxylic acid may be any alkylaromatic hydrocarbon having one or more alkyl groups that can be oxidized to a carboxylic acid group. The aromatic portion of the alkylaromatic hydrocarbon may contain one or more benzene or naphthalene nuclei with the oxidizable alkyl groups pendant from the aromatic nuclei. The pendant oxidizable alkyl groups include methyl, ethyl, n-propyl, isopropyl, n-butyl, isobutyl, secondary butyl and $C_5$ alkyl groups. Preferred alkylaromatics include toluene, ethylbenzene, m-xylene, p-xylene, o-xylene, mesitylene, pseudocumene, 3,5-dimethyl-t-butylbenzene, durene, 1,5-, 2,6- and 2,7-dimethylnaphthalene, 2,6-diethylnaphthalene, 2,6-diisopropylnaphthalene, 4,4′-dimethyldiphenylether, 3,3′,4,4′-tetramethyldiphenylether, dixylylpropane, and the like. Pseudocumene and durene are the most preferred alkylaromatics for the method of this invention and they are oxidized to trimellitic acid and pyromellitic acid, respectively.

Suitable solvents for the oxidation of alkylaromatics include any $C_2$–$C_6$ aliphatic carboxylic acid such as acetic acid, propionic acid, n-butyric acid, isobutyric acid, n-valeric acid, trimethylacetic acid and caproic acid and mixtures of one or more of these acids or a mixture of one or more of these acids with water. Preferably, the solvent is acetic acid or a mixture of acetic acid and about 0.5 to about 20 weight percent water.

The oxygen containing gas used for the oxidation of alkylaromatics in the method of this invention may vary in molecular oxygen contact from that of 1% oxygen by volume to pure oxygen gas. Air is the preferred oxygen-containing gas. The oxygen-containing gas is introduced into the oxidation reaction mixture and preferably at a point below the lowermost impeller on the agitator.

Suitable catalysts for use in the oxidation of alkylaromatics by the method of this invention include any heavy-metal catalyst or combination of catalysts conventionally used for the liquid phase oxidation of alkylaromatics. Typically, these heavy-metal catalysts are selected from the metals having an atomic number not greater than 84. Preferably, the heavy-metal catalyst comprises manganese and cobalt components added to the reaction mixture in a soluble form such as cobalt and manganese acetate or other carboxylate, or as bromide salts. The preferred catalyst for the method of this invention also comprises a source of bromine in addition to the cobalt and manganese components. Sources of bromine include elemental bromine, or ionic bromide such as hydrogen bromide, sodium bromide, potassium bromide, ammonium bromide, etc., or organic bromides which are known to provide bromide ions at the operating temperatures of the oxidation reaction. Suitable sources of organic bromides include benzylbromide, mono- and di-bromo acetic acid, ethylene dibromide, tetrabromoethane, etc.

When the oxidation catalyst comprises soluble forms of cobalt, manganese and bromine, the cobalt, calculated as elemental cobalt, is present in the range of about 0.1 to about 50 milligram atoms (mga) per gram mole of alkylaromatic hydrocarbon compound; manganese, calculated as elemental manganese, is present in the ratio of about 0.1 to about 50.0 mga per mga of cobalt, calculated as elemental cobalt; and bromine, calculated as bromine ion, is present in the ratio of about 0.1 to about 4.0 mga per mga of total cobalt and manganese, both calculated as elemental metals.

The catalyst components, including bromine, the alkylaromatic hydrocarbon, the oxygen-containing gas and the reaction solvent may be added all at once as an initial charge to the reactor vessel, or one or more of these components may be added in stages or continuously throughout the course of the oxidation reaction.

The reaction temperature is a temperature sufficient to effect the oxidation reaction of the alkylaromatic hydrocarbon to the corresponding aromatic carboxylic acid. Reaction temperature may be kept at a fixed level throughout the oxidation reaction or it may be varied as by continuously increasing the reaction temperature for a part of or for the total reaction time. Preferably the reaction temperature is in the range of about 100° C. (212° F.) to about 300° C. (572° F.) and more preferably in the range of about 150° C. (302° F.) to about 250° C. (482° F.). Reaction time is the amount of time sufficient to convert at least a portion of the alkylaromatic hydrocarbon to the corresponding aromatic carboxylic acid. Preferably, the reaction time is the amount of time required to obtain a desirable conversion of the alkylaromatic hydrocarbon to the corresponding aromatic carboxylic acid. Reaction times are typically in the range of about 0.25 hour to about 4 hours and preferably about 0.5 hour to about 1 hour.

Oxidation reaction pressure for oxidizing alkylaromatics should be sufficient to maintain at least a portion of the reaction mixture in the liquid phase. Preferably, at least about 70% of the reaction mixture charged to the oxidation reactor remains in the liquid phase.

The method of this invention wherein an alkylaromatic hydrocarbon is oxidized to a corresponding aromatic carboxylic acid can be performed in either a batch, semi-continuous, staged or continuous manner. By batch, it is meant that all of the reaction mixture components are charged initially, all at once. By semi-continuous it is meant that one or more of the reaction mixture components are charged during part or all of the reaction. By staged it is meant one or more of the reaction mixture components are charged at a specific time during the reaction. By continuous it is meant that the reaction mixture components are continuously added to the reaction mixture or reaction zone and a product stream is continuously being removed from the reaction mixture or zone. Batch, staged and semi-continuous modes of operation are the most preferred for the method of this invention.

Suitable methods for oxidizing alkylaromatics are also disclosed in U.S. Pat. Nos. 4,537,978; 4,587,350; 4,719,311; 4,755,622; 4,764,639; 4,769,488; 4,786,753; 4,816,601; 4,845,274; 4,845,275 and 4,876,385, and in U.S. patent application Ser. No. 043,838 filed Apr. 28, 1987, the specifications of which are all hereby specifically incorporated by reference.

While the preferred method of this invention has been described in the context of a liquid phase oxidation reaction wherein there is present a liquid phase, a gaseous phase and possibly a solid phase and wherein it has unexpectedly been found that improved mixing is provided by maintaining constant mixing power, it should be readily apparent to those skilled in the art that the method of this invention is applicable to any chemical reaction or mixing apparatus wherein it is desirable to provide and maintain efficient mixing. This is particularly true where the composition of the material being mixed changes in property such as viscosity or, as described above, density, during the mixing period.

The following example illustrates the advantages that are achieved using improved mixing during the oxidation of an alkylaromatic hydrocarbon to an aromatic carboxylic acid in the liquid phase. This example is not, however, to be construed as limiting the scope of the invention since it will be readily apparent to those of skill in the art that modifications and variations may be made in the practice of this invention.

EXAMPLE

A series of 19 test oxidation reactions were conducted wherein pseudocumene was oxidized to trimellitic acid using air as the source of oxygen-containing gas, acetic acid as the reaction solvent and a catalyst package containing cobalt, manganese, zirconium and bromine components. The oxidation reactor was equipped with a variable speed electric motor for rotating the agitator. The agitator had two turbines, each turbine equipped with 6 flat blades and a disk. The air was introduced into the reactor from a single source below the lowermost turbine throughout the approximately 50 minute reaction. Each of the 19 runs were run under the same conditions except that 14 runs were conducted with the amp controller set so that the input to the electric motor was maintained at 28 amps during the oxidation reaction while for the remaining 5 runs, the electric motor was run with the amp controller set at 37 amps during the course of the oxidation reaction. Automatic constant amp control was maintained by altering mixing speed. At 28 amps, the nominal agitator speed was 84 rpm. At 37 amps the nominal agitator speed was 116 rpm. During the course of each reaction, the reactor vent-gas stream was analyzed for oxygen content. The average oxygen concentrations for the runs made at 28 and 37 amps are reported in Table 1 as a function of reaction time.

TABLE 1

| Reaction Time (minutes) | Average O$_2$ in Reactor Vent (% O$_2$) | |
| --- | --- | --- |
|  | 28 amps[1] | 37 amps[2] |
| 1 | 0.3 | 0.0 |
| 5 | 3.2 | 1.3 |
| 10 | 2.2 | 1.0 |
| 15 | 2.7 | 1.3 |
| 20 | 4.8 | 2.4 |
| 25 | 6.0 | 2.7 |
| 30 | 7.3 | 3.2 |
| 35 | 4.7 | 1.9 |
| 40 | 1.8 | 1.5 |
| 45 | 1.8 | 3.3 |
| 47 | 3.6 | 8.5 |
| 50 | 10.5 | — |
| 52 | 12.7 | — |

[1]Average data from 14 runs.
[2]Average data from 5 runs.

The data in Table 1 conclusively shows that improved mixing improves the oxidation of an alkylaromatic hydrocarbon to an aromatic carboxylic acid. For the runs made at the higher constant amperage the oxygen concentration in the reactor vent gas was considerably lower throughout the oxidation reaction than the oxygen concentration in the vent gas for the runs made at the lower amperage. This clearly indicates that for the runs made at the higher amperage, the oxygen is being consumed more effectively. Additionally, the data in Table 1 shows that the rapid increase in vent gas oxygen concentration signifying the end of the oxidation reaction occurs 3-5 minutes earlier in the runs made at 37 amps compared to the runs made at 27 amps. This shortened reaction time is a further indication that improved mixing results in a more efficient liquid phase oxidation reaction.

What is claimed is:

1. An improved method for oxidizing an oxidizable component in the liquid phase with an oxygen containing gas phase component, the improvement comprising mixing the liquid phase and the gas phase in a reactor with a rotating agitator element wherein said agitator is rotated by a means for providing variable rotation speeds, and wherein said means for providing variable rotation speeds, and wherein said means for providing variable rotation speed is maintained at substantially constant power.

2. A method for oxidizing an alkylaromatic hydrocarbon to a corresponding aromatic carboxylic acid in the liquid phase under oxidation reaction conditions comprising, introducing into a suitable oxidation reactor a reaction mixture comprising a suitable reaction solvent, an oxidation catalyst comprising heavy-metal components, said alkylaromatic hydrocarbon, and an oxygen-containing gas; mixing said reaction mixture; and maintaining said reaction mixture at a temperature and for a time sufficient to convert at least a portion of said alkylaromatic hydrocarbon to said carboxylic acid; wherein said mixing comprises rotating an agitator element located within said reaction mixture with a means for providing variable rotation speeds, and wherein said means for providing variable rotation speeds is maintained at substantially constant power during at least a substantial portion of said addition of said oxygen-containing gas.

3. The method of claim 1 wherein said agitator is rotated by a variable speed electric motor.

4. The method of claim 2 wherein said agitator element is rotated by a variable speed electric motor.

5. The method of claim 4 wherein said oxygen-containing gas is air, said oxidation catalyst comprises cobalt, manganese and bromine components, and said reaction solvent comprises acetic acid.

6. The method of claim 5 wherein said alkylaromatic hydrocarbon is pseudocumene and said aromatic carboxylic acid is trimellitic acid.

7. The method of claim 5 wherein said alkylaromatic hydrocarbon is durene and said aromatic carboxylic acid is pyromellitic acid.

8. The method of claim 3 wherein said substantially constant power is maintained by maintaining substantially constant amperage to said variable speed electric motor.

9. The method of claim 4 wherein said substantially constant power is maintained by maintaining substantially constant amperage to said variable speed electric motor.

10. The process of claim 2 wherein the oxidizing is performed in a batch manner.

11. The process of claim 2 wherein the oxidizing is performed in a semi-continuous manner.

12. The process of claim 2 wherein the oxidizing is performed in a staged manner.

* * * * *

UNITED STATES PATENT OFFICE
CERTIFICATE OF CORRECTION

Patent No. 5,095,143  Dated 3-10-92

Inventor(s) Heberer et al.

It is certified that error appears in the above-identified patent and that said Letters Patent is hereby corrected as shown below:

Column 10    lines 4-5, "rotation speeds, and wherein said means for providing variable rotation speed is maintained" should read --rotation speed is maintained--

Signed and Sealed this

Eighth Day of September, 1992

Attest:

DOUGLAS B. COMER

Attesting Officer    Acting Commissioner of Patents and Trademarks